United States Patent
Mueller

[19]

[11] Patent Number: 6,001,305
[45] Date of Patent: Dec. 14, 1999

[54] STERILIZER WITH ELLIPTICAL PRESSURE VESSEL

[75] Inventor: Wolfgang Mueller, Erie, Pa.

[73] Assignee: Steris Corporation, Mentor, Ohio

[21] Appl. No.: 09/076,578

[22] Filed: May 12, 1998

[51] Int. Cl.[6] .................................. A61L 2/08; A61L 9/00
[52] U.S. Cl. ................................. 422/26; 422/1; 422/295; 422/296
[58] Field of Search .................................. 422/1, 26, 292, 422/295, 296, 297

[56] References Cited

U.S. PATENT DOCUMENTS

| | | |
|---|---|---|
| 1,409,286 | 3/1922 | Diner . |
| 3,407,027 | 10/1968 | Huston ........................................ 21/91 |
| 3,415,613 | 12/1968 | Wallden ...................................... 21/56 |
| 4,228,134 | 10/1980 | Alfio ........................................ 422/208 |
| 4,974,663 | 12/1990 | Nakaji ...................................... 422/295 |
| 5,059,392 | 10/1991 | Wijts ........................................ 422/302 |
| 5,119,994 | 6/1992 | Placzek ..................................... 241/17 |
| 5,213,775 | 5/1993 | Ghiretti .................................... 422/295 |
| 5,217,688 | 6/1993 | Von Lersner ............................. 422/295 |
| 5,840,248 | 11/1998 | Ongaro ...................................... 422/26 |

FOREIGN PATENT DOCUMENTS

| | | |
|---|---|---|
| 1 805 985 | 9/1970 | Germany . |
| 3639371A1 | 5/1988 | Germany . |

*Primary Examiner*—Krisanne Thornton
*Attorney, Agent, or Firm*—Fay, Sharpe, Fagan, Minnich & McKee, LLP

[57] ABSTRACT

An elliptical steam sterilizer includes an elliptically shaped inner shell (12) and an elliptically shaped outer jacket (14). The inner shell (12) and outer jacket (14) are supported on opposite ends by an end plate (16) and a back head (20). The elliptical shape of the sterilizer distributes the forces caused by pressurization and evacuation of the inner shell (12) in a beneficial manner which eliminates the need for expensive reinforcement of the inner shell and outer jacket (14). The elliptical shape, which is oriented with its major axis (Y) positioned vertically and its minor axis (X) positioned horizontally, provides greater capacity than a cylindrical sterilizer with the same size footprint.

20 Claims, 4 Drawing Sheets

STERILIZER WITH ELLIPTICAL PRESSURE VESSEL

BACKGROUND OF THE INVENTION

The present invention relates to the field of pressure vessels. It finds particular application to sterilizers or autoclaves for steam sterilization of medical and laboratory instruments and other equipment. It is to be appreciated, however, that the present invention may also find application in conjunction with other types of sterilizing, disinfecting, and sanitizing apparatus.

Steam sterilizers are currently used in hospitals, doctors offices, dentists offices, and laboratories to sterilize medical and dental instruments, laboratory equipment, production equipment, manufactured products, and other equipment. Sterilizers are made in different sizes for different applications from 6–10 liter small size sterilizers which fit a few trays of instruments and can be used in a small doctor's or dentist's office to large sterilizers which are the size of a small room. In between these two extremes are sterilizer sizes typically used in hospitals to sterilize everything used with patients, including linens, bedding, bed pans, as well as medical instruments.

Steam sterilizers generally include an inner shell which defines a sterilization chamber into which the articles to be sterilized are placed. The sterilizers may also include an outer jacket surrounding the inner shell and providing a space between the inner shell and outer jacket for injection of steam. The sterilizers are operated by placing the articles to be sterilized inside the chamber and preheating the chamber by pumping saturated steam into the jacket space between the outer jacket and the inner shell. Once the jacket is charged with steam, saturated steam is injected into the sterilization chamber. Commonly, in hospital applications, steam is piped from inside the jacket space into the sterilization chamber for sterilizing the chamber contents.

At the end of the sterilization cycle, the steam is pumped out of the chamber and the chamber evacuated to a pressure below atmospheric pressure to remove any moisture remaining in the chamber or on the sterilized articles.

Small and medium size sterilizers are generally either cylindrical or rectangular in shape. There is a trade off between usable space and manufacturing cost between cylindrical and rectangular sterilizers. The cylindrical sterilizers are less expensive to manufacture due to their shape which meets stress/strain requirements for pressurization without additional reinforcing structures surrounding the cylinder. However, cylindrical sterilizers include some amount of unusable space because the items placed in the sterilizer are generally rectangular. In contrast, rectangular sterilizers provide more usable space than cylindrical sterilizers for the same size of foot print. The cost of rectangular sterilizers is generally greater than that of cylindrical sterilizers of the same size due to reinforcement which is needed particularly at the corners of the rectangular sterilizer shell to provide sufficient shell strength.

The present invention contemplates a new and improved sterilizer for addressing the capacity versus cost tradeoff of known sterilizers.

SUMMARY OF THE INVENTION

In accordance with one aspect of the present invention, a device for sterilizing includes an inner shell having an elliptical cross section, an outer jacket surrounding the inner shell also having an elliptical cross section, a front wall, and a back wall. A sterilization chamber is defined by the inner shell, a front closure, and a back wall. A first inlet pipe delivers steam to the sterilization chamber. A preheating space is defined between the inner shell and the outer jacket, and a second inlet pipe delivers steam to the preheating space to preheat the sterilization chamber.

In accordance with a more limited aspect of the present invention, the inner shell and outer jacket have a major diameter positioned vertically and a minor diameter positioned horizontally.

In accordance with another more limited aspect of the invention, the inner and outer shells are supported on a support structure.

One advantage of the present invention resides in an increased capacity for a given footprint relative to cylindrical steam vessel sterilizers.

Another advantage resides in economical manufacturing costs and reduced reinforcement relative to rectangular steam vessel units.

Still other advantages and benefits of the invention will become apparent to those skilled in the art upon a reading and understanding of the following detailed description.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENT

Figure 1:
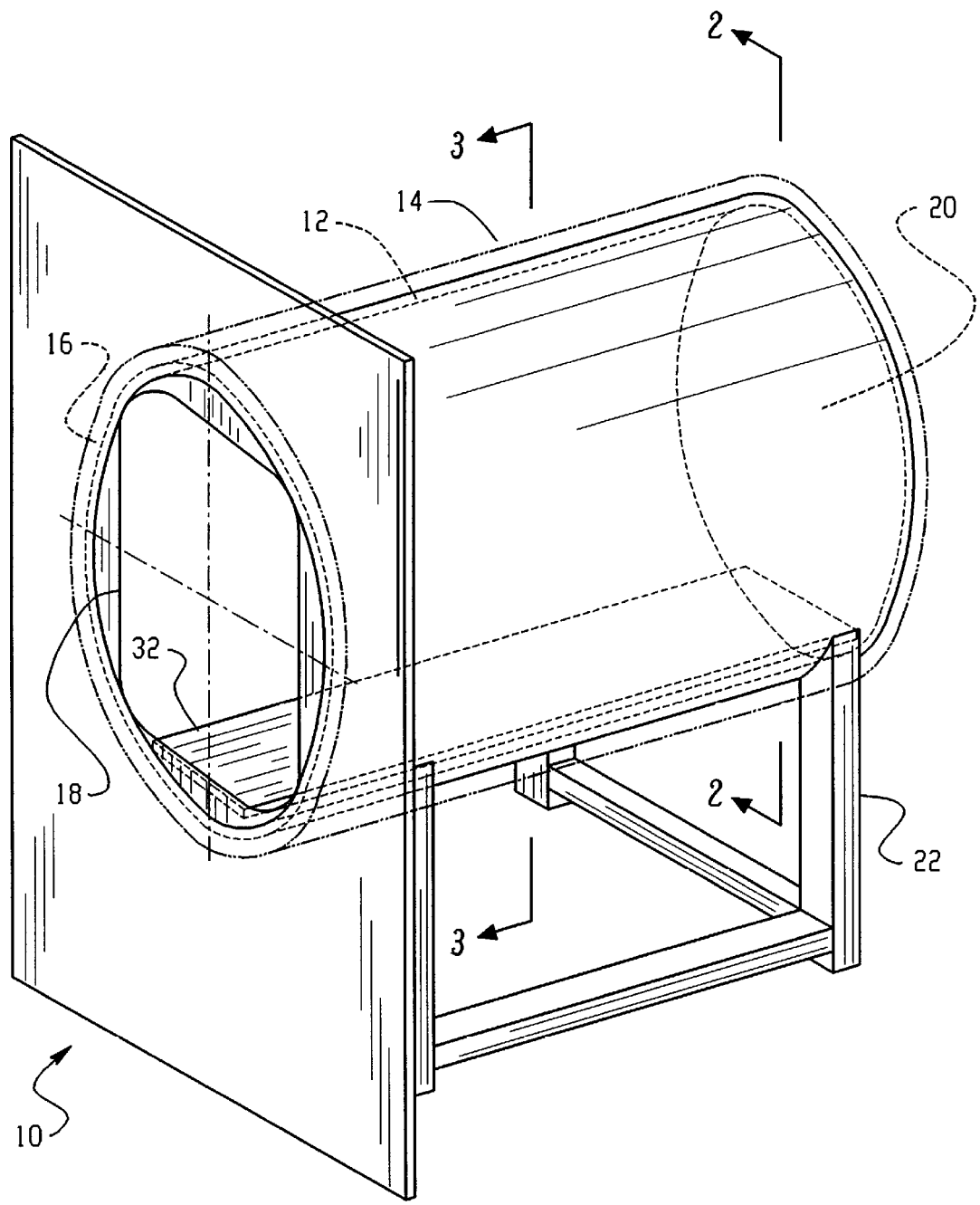
FIG. 1 is a perspective view of the elliptical sterilizer.
Figure 2:
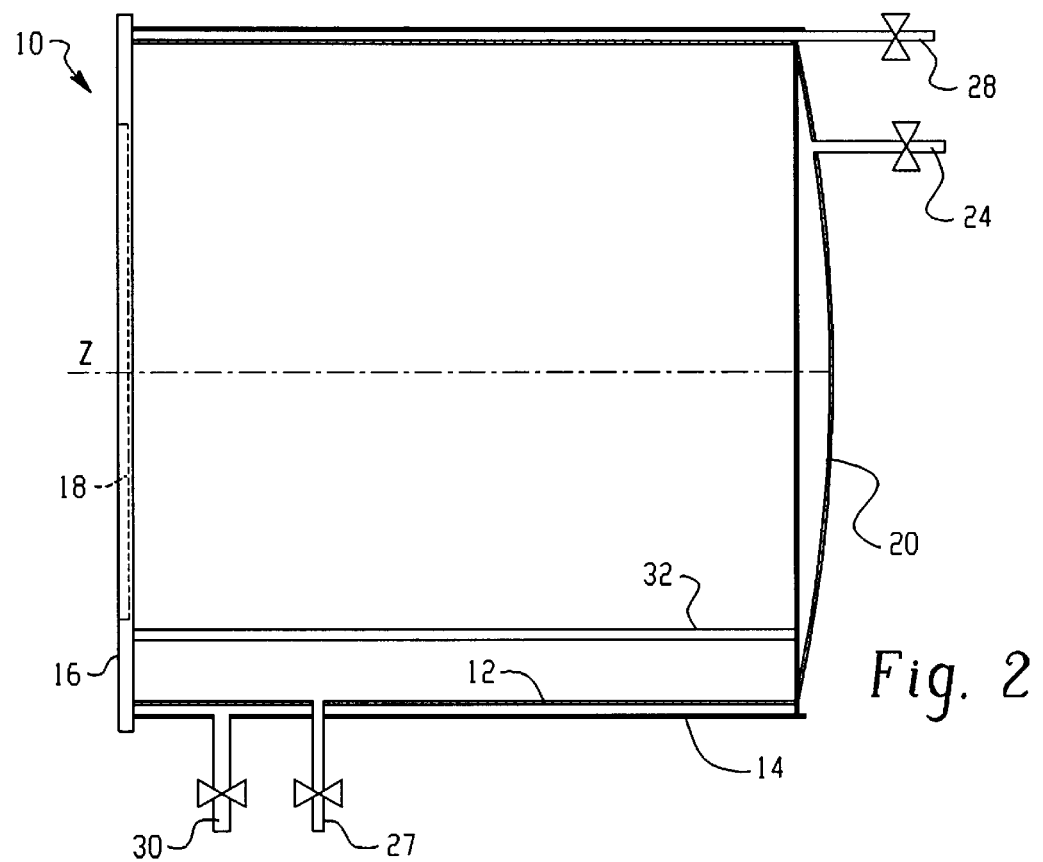
FIG. 2 is a cross sectional side view of the elliptical sterilizer taken along line 2—2 of FIG. 1; a FIG. 3 is a cross sectional view of the elliptical sterilizer taken along line 3—3 of FIG. 1.
Figure 3:
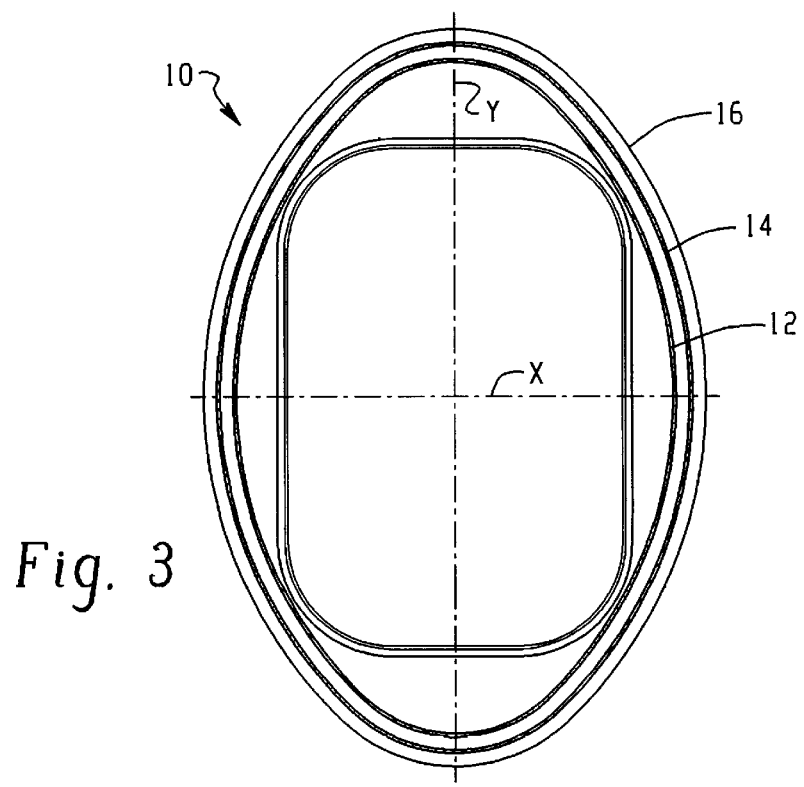

With reference to FIGS. 1–3, an elliptical steam sterilizer 10 includes an inner shell 12, an outer jacket 14, an end plate 16 having an opening 18, and a back head 20. The inner shell, end plate, and back head define a chamber. The sterilizer 10 is supported on a support structure or frame 22. The inner shell 12 and the outer jacket 14 are elliptical in cross section as shown in FIG. 2 with a major axis or diameter Y of the ellipse positioned vertically and a minor axis or diameter X positioned horizontally. The major and minor diameters preferably have a ratio of between about 1.2:1 and 2.5:1, with a particularly preferred ratio of between 1.4:1 and 1.5:1.

The elliptical inner shell 12 is formed from a single plate of stainless steel or other non-corrosive material. The elliptical shape may be derived from a simple ellipse or from an approximate ellipse, constructed geometrically from a series of circular arcs. Preferably, the plate is rolled to an elliptical shape using a rolling machine and then welded together along two opposite ends of the plate. Alternatively, the plate is rolled, welded together along two opposite ends to form a cylinder and expanded to the desired elliptical shape. A Grotnes expander may be used to expand the plate to the final elliptical shape. According to one embodiment, a plurality of gussets are then welded onto the inner shell 12 to facilitate the positioning and fit of the outer jacket 14.

The elliptical outer jacket 14 is formed from stainless steel or other material in the same manner as the inner shell 12. According to one embodiment, a backer strip is welded to the stainless steel plates of the shell 12 and jacket 14 prior to welding the edges together to achieve an improved weld joint. The inner shell 12 and outer jacket 14 are preferably about 4–8 mm thick.

The elliptical cross-sectional shapes of the inner shell 12 and the outer jacket 14 have a major diameter (largest diameter) and a minor diameter (smallest diameter). The minor diameter is between 40% and 90%, preferably between 55% and 75%, of the major diameter. According to one example of the steam sterilizer 10, the major diameter of the inner shell 12 is about 135 cm and the minor diameter is about 88 cm. The space between the inner shell 12 and the outer jacket 14 is between 5 and 125 mm, preferably about 13 mm. The sterilizer is made in different lengths to provide varying sterilization capacity.

The end plate 16 is a flat elliptically, or rectangularly shaped plate which is formed from one, two, or four pieces, welded together, depending on a size of the sterilizer. The end plate 16 is dimensioned to be somewhat larger than the elliptical outer jacket 14 such that the ends of the inner shell 12 and outer jacket are welded to the end plate. The end plate 16 is preferably about 25 mm thick and includes a rectangular opening 18 with rounded corners.

A door is provided which is sealed to the edges of the opening 18 in a known leak-tight manner. The door seal is capable of withstanding the pressures prevailing inside the sterilizing chamber. The door is either a sliding door or a hinged door as is known in the art.

According to an alternative embodiment, the back head 20 is replaced by a second end plate and doors are provided on both end plates for two ended loading and unloading of the pressure vessel.

The back head 20 is dish shaped with a peripheral flat flange. An end of the inner shell 12 is welded along the flange. Optionally, positioning elements are welded to the flange, inner shell, or outer jacket to assist in relative positioning of the back head and jacket during welding. In one embodiment, the back head has an outer, elliptically-shaped periphery which fits into the second end of the outer jacket 14.

Figure 4:
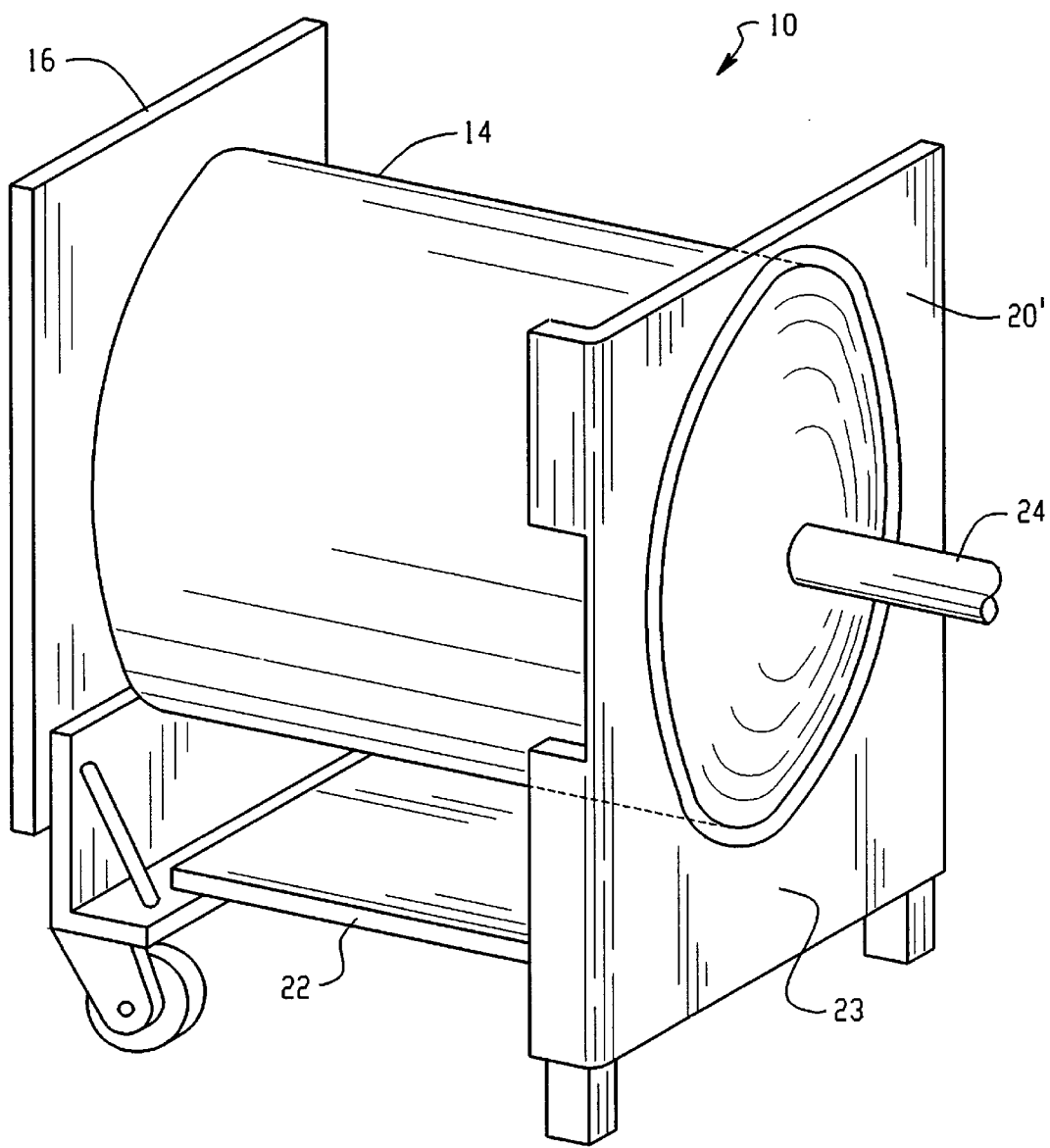
FIG. 4 is a perspective view of an alternative embodiment of the elliptical sterilizer of the present invention; and, FIG. 5 is a cross sectional side view of a second alternative embodiment of the elliptical sterilizer.

FIG. 4 shows an alternative embodiment, in which the back head 20' is larger than the outer jacket and optionally has a rectangular periphery. In this way, a lower extending portion 23 of the back head forms part of the support 22.

With reference to FIGS. 2 and 4, the back head 20 is welded to both the inner shell 12 and the outer jacket 14 to form a leak-proof seal with both of these members. Preferably, the back head 20, when assembled, is outwardly convex, although flat back heads are also contemplated.

High pressure steam is delivered to the sterilization chamber from a boiler or other steam generator through the back head 20 by a first steam inlet pipe 24. In a preferred embodiment, shown in FIG. 5, the steam used in the sterilizer is first passed through the space between the inner shell 12 and the outer jacket 14. This is beneficial for hospital sterilizers, in particular, because the jacket space acts to reduce the level of condensate in the steam prior to the entry of the steam into the sterilizer. A shut off valve 25 controls the passage of steam from an outlet 26 in the jacket space to the inlet pipe 24.

Figure 5:
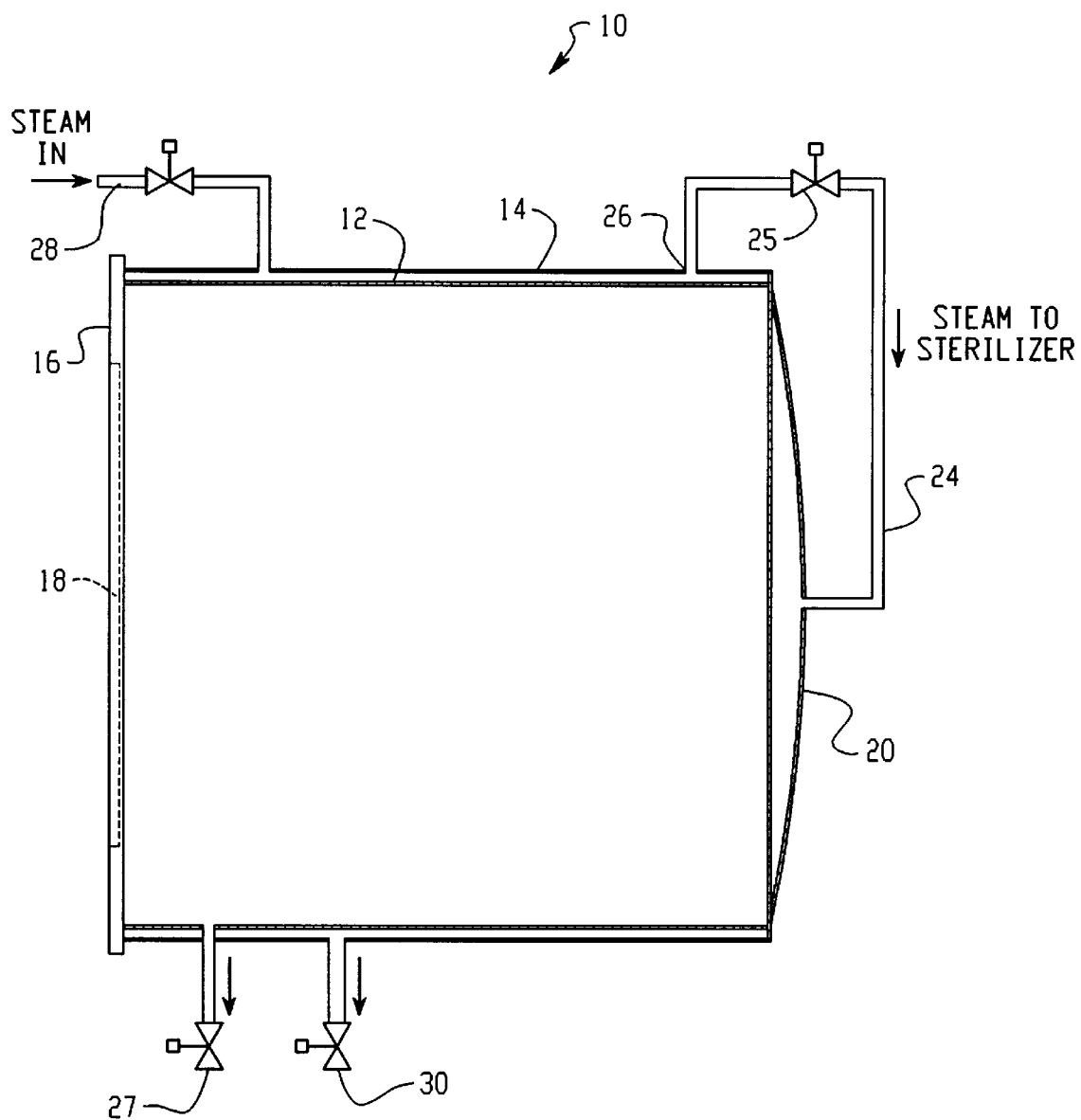

With continued reference to FIG. 5, and reference also to FIGS. 1–3, any condensation accumulating in the sterilization chamber is drained out through a drain 27 located at the bottom of the chamber. The drain 27 is connected to a source of suction, such as a vacuum pump, which is used to draw the steam out of the sterilization chamber at the end of the sterilization process so that the steam does not condense on the articles within the chamber as the chamber is cooled. A second steam inlet pipe 28 in the jacket 14 and a second drain 30 in the bottom of the jacket 14 are provided for pressurizing and draining the jacket space between the inner shell 12 and the outer jacket 14.

According to one embodiment, the sterilizer includes one or more shelves which are removably mounted within the inner shell 12 for placing articles to be sterilized within the sterilization chamber. A bottom shelf 32 is positioned horizontally either level with or just below a bottom edge of the opening 18. The remainder of the shelves are preferably removable so that a plurality of smaller articles can be placed on these shelves for sterilization or the shelves can be removed to accommodate larger articles. The shelves are wire or punched sheets to allow the steam to pass through to provide even heating of the articles within the chamber and to minimize heat loading.

In an alternative embodiment, articles to be sterilized are loaded onto a cart which remains in the sterilization chamber during sterilization and is then removed along with the sterilized articles.

The elliptical shape of the inner shell 12 allows the forces caused by pressurization of the chamber to be relatively evenly distributed to the walls of the chamber and prevents weak spots which occur in rectangular pressure vessels requiring reinforcement. The support of the inner shell 12 at the two ends by the end plate 16 and back head 20 provides sufficient strength to sustain the pressures of sterilization for shell lengths typically employed in sterilizers for hospital use.

The elliptical sterilizer shell is economical to manufacture in terms of number of components, operations, and complexity of assembly. The elliptical sterilizer also provides increased capacity for the same footprint or floor area which is taken up by a cylindrical sterilizer.

In addition, the elliptical sterilizer eliminates the need for extensive structural braces between the inner shell and outer jacket which are needed in rectangular sterilizers.

The invention has been described with reference to the preferred embodiments thereof. Obviously, modifications and alterations will occur to others upon a reading and understanding of the preceding detailed description. It is intended that the invention be construed as including all such modifications and alterations insofar as they come within the scope of the appended claims or their equivalents.

Having thus described the preferred embodiment, the invention is now claimed to be:

1. A steam autoclave comprising:
   an inner shell having an elliptical cross section;
   an outer jacket surrounding the inner shell;
   an end plate connected to the inner shell and outer jacket;
   a back head connected to the inner shell and the outer jacket such that a space is defined between the inner shell, the outer jacket, the end plate, and the back head;
   a chamber defined by the inner shell, the end plate, and the back head;
   a first inlet pipe for delivering steam to the chamber; and
   a second inlet pipe for delivering steam to the space between the inner shell and outer jacket.

2. The autoclave as set forth in claim 1 wherein the end plate includes a substantially rectangular opening with a door.

3. The autoclave as set forth in claim 1 wherein the inner shell has a major diameter which is positioned vertically.

4. The autoclave as set forth in claim 3 wherein the inner shell has a minor diameter which is positioned horizontally.

5. The autoclave as set forth in claim 4 wherein the outer jacket has an elliptical cross section.

6. The autoclave as set forth in claim 4 wherein the inner shell and outer jacket are supported on a support structure.

7. The autoclave as set forth in claim 6 wherein the back head forms part of the support structure.

8. The autoclave as set forth in claim 1 further including a shelf mounted within the inner shell.

9. The autoclave as set forth in claim 1 wherein the inner shell has a major diameter and a minor diameter, and wherein the minor diameter is between 40% and 90% of the major diameter.

10. The autoclave as set forth in claim 9 wherein the major diameter is from about 1.4 to 1.5 times the minor diameter.

11. The autoclave as set forth in claim 1 wherein the second inlet pipe is fluidly connected to an outlet in the jacket, whereby steam is passed first through the space and then to the chamber.

12. A steam autoclave comprising:

an elliptical sterilization chamber having a major axis and a minor axis, a diameter of the sterilization chamber along the major axis being larger than a diameter of the sterilization chamber along the minor axis; and a support structure supporting the elliptical sterilization chamber with the major axis oriented vertically.

13. The autoclave as set forth in claim 12 wherein the sterilization chamber is formed by an elliptical inner shell, the elliptical inner shell being surrounded by an elliptical outer jacket.

14. The autoclave as set forth in claim 12 further including a preheating means for delivering preheating fluid to a space between the inner shell and the outer jacket.

15. The autoclave as set forth in claim 12 wherein the diameter of the sterilization chamber along the minor axis is between 40% and 90% of the diameter of the sterilization chamber along the major axis.

16. In an autoclave including an inner shell defining a sterilization chamber, an outer jacket surrounding the inner shell and spaced from the inner shell to form a jacket space for circulating preheating fluid to preheat the sterilization chamber, and an opening for placing articles to be sterilized into the sterilization chamber, the improvement comprising:

the inner shell and the outer jacket being elliptical in cross section.

17. The autoclave as set forth in claim 16 wherein the inner shell has a major diameter which is positioned vertically and a minor diameter which is positioned horizontally.

18. The autoclave as set forth in claim 17 wherein the minor diameter is between 40% and 90% of the major diameter.

19. A method of sterilization comprising:

placing articles to be sterilized into an elliptical shaped sterilization chamber;

preheating the sterilization chamber by injecting a preheating fluid into a substantially elliptical annular space surrounding the elliptically shaped sterilization chamber; and sterilizing the articles in the sterilization chamber by injecting heated steam into the elliptical shaped sterilization chamber.

20. The method as set forth in claim 19 further including evacuating the steam from the elliptical sterilization chamber before removing the articles from the sterilization chamber.

* * * * *